US010092646B2

(12) United States Patent
Grossman et al.

(10) Patent No.: US 10,092,646 B2
(45) Date of Patent: Oct. 9, 2018

(54) COMPOSITIONS AND METHODS FOR BETA-GLUCAN IMMUNOTHERAPY

(71) Applicant: Biothera, Inc., Eagan, MN (US)

(72) Inventors: William J. Grossman, Third Lake, IL (US); Mary A. Antonysamy, Woodbury, MN (US); Richard M. Walsh, Lino Lakes, MN (US); Mariana I. Nelson, Rosemount, MN (US); Nandita Bose, Plymouth, MN (US); Michael E. Danielson, St. Paul, MN (US); Kyle S. Michel, Eagan, MN (US)

(73) Assignee: Biothera, Inc., Eagan, MN (US)

( * ) Notice: Subject to any disclaimer, the term of this patent is extended or adjusted under 35 U.S.C. 154(b) by 637 days.

(21) Appl. No.: 14/398,020

(22) PCT Filed: Mar. 14, 2013

(86) PCT No.: PCT/US2013/031625
§ 371 (c)(1),
(2) Date: Oct. 30, 2014

(87) PCT Pub. No.: WO2013/165593
PCT Pub. Date: Jul. 11, 2013

(65) Prior Publication Data
US 2015/0125451 A1    May 7, 2015

Related U.S. Application Data

(60) Provisional application No. 61/640,842, filed on May 1, 2012, provisional application No. 61/640,834, filed on May 1, 2012, provisional application No. 61/640,397, filed on Apr. 30, 2012.

(51) Int. Cl.
| | |
|---|---|
| *C07H 1/00* | (2006.01) |
| *A61K 39/00* | (2006.01) |
| *A61K 39/40* | (2006.01) |
| *A61K 39/395* | (2006.01) |
| *A61K 31/716* | (2006.01) |
| *C07K 16/12* | (2006.01) |
| *C07K 16/14* | (2006.01) |
| *A61K 45/06* | (2006.01) |
| *A61K 39/39* | (2006.01) |
| *G01N 33/569* | (2006.01) |
| *A61K 47/68* | (2017.01) |

(52) U.S. Cl.
CPC ...... *A61K 39/39583* (2013.01); *A61K 31/716* (2013.01); *A61K 39/39* (2013.01); *A61K 39/39558* (2013.01); *A61K 39/39575* (2013.01); *A61K 45/06* (2013.01); *A61K 47/6835* (2017.08); *C07K 16/12* (2013.01); *C07K 16/14* (2013.01); *G01N 33/56966* (2013.01); *A61K 2039/55583* (2013.01); *G01N 2400/24* (2013.01)

(58) Field of Classification Search
None
See application file for complete search history.

(56) References Cited

U.S. PATENT DOCUMENTS

| | | | |
|---|---|---|---|
| 6,204,366 B1 | 3/2001 | Verhoeyen | |
| 6,294,321 B1 | 9/2001 | Wakshull et al. | |
| 6,355,625 B1 | 3/2002 | Pavliak et al. | |
| 7,981,447 B2 | 7/2011 | Cox | |
| 2001/0051717 A1 | 12/2001 | Wakshull et al. | |
| 2004/0014715 A1 | 1/2004 | Ostroff | |
| 2006/0009419 A1 | 1/2006 | Ross et al. | |
| 2008/0103112 A1 | 5/2008 | Magee et al. | |
| 2010/0297130 A1 | 11/2010 | Cassone et al. | |
| 2015/0125461 A1 | 5/2015 | Grossman et al. | |

FOREIGN PATENT DOCUMENTS

| | | | |
|---|---|---|---|
| CN | 1694715 A | 11/2005 | |
| CN | 1697659 A | 11/2005 | |
| CN | 1723027 A | 1/2006 | |
| CN | 1823092 A | 8/2006 | |
| CN | 1964722 A | 5/2007 | |
| EP | 1 891 970 A1 | 2/2008 | |
| EP | 1 506 009 B1 * | 5/2008 | .......... A61K 39/385 |
| JP | 2002-508518 A | 3/2002 | |
| JP | 2005-535298 A | 11/2005 | |
| JP | 2007-155334 A | 6/2007 | |

(Continued)

OTHER PUBLICATIONS

European Patent Application No. 13784472, filed Mar. 14, 2013; Extended European Search Report dated Nov. 27, 2015; 11 pages.
European Patent Application No. 13784589, filed Mar. 14, 2013; Extended European Search Report dated Nov. 27, 2015; 13 pages.
PCT Patent Application No. PCT/US2013/031606, filed Mar. 14, 2013; International Preliminary Report on Patentability issued on Nov. 13, 2014; 7 pages.
PCT Patent Application No. PCT/US2013/031606, filed Mar. 14, 2013; International Search Report/Written Opinion dated Jun. 4, 2013; 9 pages.
PCT Patent Application No. PCT/2013/031625, filed Mar. 14, 2013; International Preliminary Report on Patentability dated Nov. 13, 2014; 8 pages.
PCT Patent Application No. PCT/2013/031625, filed Mar. 14, 2013; International Search Report/Written Opinion dated May 17, 2013; 10 pages.

(Continued)

*Primary Examiner* — Nora M Rooney
(74) *Attorney, Agent, or Firm* — Mueting, Raasch & Gebhardt P.A.

(57) ABSTRACT

This disclosure describes, in one aspect, a composition that includes a β-glucan component and an antibody component that specifically binds to the β-glucan. In another aspect, this disclosure describes a method of increasing a subject's response to β-glucan immunotherapy. Generally, the method includes identifying the subject as a low binder of β-glucan and administering to the subject a composition that comprises a β-glucan moiety conjugated to the therapeutic antibody. In some cases, the therapeutic antibody can be an anti-tumor antibody.

13 Claims, 6 Drawing Sheets

(56) References Cited

FOREIGN PATENT DOCUMENTS

| | | |
|---|---|---|
| JP | 2009-528267 A | 8/2009 |
| WO | WO 99/31510 A1 | 6/1999 |
| WO | WO 03/097091 A2 | 11/2003 |
| WO | WO 2004/021994 A2 | 3/2004 |
| WO | WO 2004/030613 A2 | 4/2004 |
| WO | WO 2005/018544 A2 | 3/2005 |
| WO | WO 2006/085895 A2 | 8/2006 |
| WO | WO 2007-084661 A2 | 7/2007 |
| WO | WO 2009/134891 A2 | 11/2009 |
| WO | WO 2012/154680 A2 | 11/2012 |
| WO | WO 2012/154818 A1 | 11/2012 |
| WO | WO 2013/165591 A1 | 11/2013 |
| WO | WO 2013/165593 A1 | 11/2013 |

OTHER PUBLICATIONS

Antonysamy et al., "Differential Neutrophil Binding of Imprime PGG®, a β-1,3/1,6 Immunomodulatory Glucan", Jun. 9-12, 2012, *International Symposium the Neutrophil in Immunity*, Research Abstract, 1 pages.

Bose et al., "Binding of soluble yeast β-glucan to human neutrophils and monocytes is complement-dependent", Aug. 12, 2013, *Frontiers in Immunology*, 4(230):1-14.

Deslandes et al., "Triple-Helical Structure of (1→3)-β-D-Glucan", Nov. 1980, *Macromolecules*, 13(6):1466-1471.

Eberhard et al., "Mutations in the Epidermal Growth Factor Receptor and in KRAS Are Predictive and Prognostic Indicators in Patients With Non-Small-Cell Lung Cancer Treated With Chemotherapy Alone and in Combination With Erlotinib", Sep. 1, 2005, *J Clin Oncol*, 23(25):5900-5909.

Ensley et al., "NMR spectral analysis of a water-insoluble (1→3)-β-glucan isolated from *Saccharomyces cerevisiae*", May 20, 1994, *Carbohydrate Research*, 258:307-311.

Goodridge et al., "Activation of the innate immune receptor Dectin-1 upon formation of a phagocytic synapse", Apr. 28, 2011, *Nature*, 472:471-476.

Ishibashi, et al., "Influence of Anti-β-Glucan Antibody on Fungal Cell Wall β-Glucan Bioactivity", 2009, *Journal of Japanese Society for Bacteriology*, 64(1):168 (P1-240). English Translation provided. 4 pages.

Isoda et al., "Clinical Efficacy of Superfine Dispersed Lentinan (β-1,3-glucan) in Patients with Hepatocellular Carcinoma", 2009, *Hepatogastroenterology*, 56(90):437-441.

Lamm et al., "A Randomized Trial of Intravesical Doxorubicin and Immunotherapy with Bacille Calmette-Guérin for Transitional-Cell Carcinoma of the Bladder", Oct. 24, 1991, *The New England Journal of Medicine*, 325(17):1205-1209.

Li et al., "Yeast β-Glucan Amplifies Phagocyte Killing of iC3b-Opsonized Tumor Cells via Complement Receptor 3-Syk-Phosphatidylinositol 3-Kinase Pathway", 2006, *Journal of Immunology*, 177:1661-1669.

Li et al., "Combined Yeast β-Glucan and Antitumor Monoclonal Antibody Therapy Requires C5a-Mediated Neutrophil Chemotaxis via Regulation of Decay-Accelerating Factor CD55", Aug. 1, 2007, *Cancer Research*, 67:7421-7430.

Mathé et al., "Active Immuotherapy for Acute Lymphoblastic Leukemia", Apr. 5, 1969, *The Lancet*, 1(7597):697-699.

Meikle et al., "The location of (1→3)-β-glucans in the walls of pollen tubes of *Nicotiana alata* using a (1→3)-β-glucan-specific monoclonal antibody", Mar. 20, 1991, *Planta*, 185:1-8.

Morales et al., "Intracavitary Bacillus Calmette—Guerin in the treatment of superficial bladder tumors", Aug. 1976, *The Journal of Urology*, 116(2):180-183.

Noss et al., "IgG to Various Beta-Glucans in a Human Adult Population", 2012, *Int. Arch. Allergy Immunol.*, 157:98-108. First published online Sep. 7, 2011.

Oka et al., "*In Vitro* and *In Vivo* Analysis of Human Leukocyte Binding by the Antitumor Polysaccharide, Lentinan", 1996, *Int. J. Immunopharmac.*, 18(3):211-216.

Pearl, "Cancer and Tuberculosis", 1929, *American Journal of Hygiene*, 9:97-159.

Qi et al., "Differential pathways regulating innate and adaptive antitumor immune responses by particulate and soluble yeast-derived β-glucans", Jun. 23, 2011, *Blood*, 117(25):6825-6836.

Roberts et al., "Targeting the Raf-MEK-ERK mitogen-activated protein kinase cascade for the treatment of cancer", 2007, *Oncogene*, 26:3291-3310.

Rubin-Bejerano et al., "Phagocytosis by Human Neutrophils Is Stimulated by a Unique Fungal Cell Wall Component", Jul. 2007, *Cell Host & Microbe*, 2:55-67.

Ruckdeschel et al., "Postoperative Empyema Improves Survival in Lung Cancer—Documentation and Analysis of a Natural Experiment", Nov. 16, 1972, *The New England Journal of Medicine*, 287(20): 1013-1017.

Sakamoto, "Function of β-glucan", 2011, *New Food Industry*, 53(12):1-11. English translation of pp. 9-10 provided. 13 pages.

Salvador et al., "Yeast-Derived β-Glucan Augments the Therapeutic Efficacy Mediated by Anti-Vascular Endothelial Growth Factor Monoclonal Antibody in Human Carcinoma Xenograft Models", Feb. 15, 2008, *Clinical Cancer Research*, 14(4):1239-1247.

Shindo et al., "Is T1G3 Cancer Having a Definite Muscle Layer in TUR Specimens a Highly Progressive Disease?", 2010, *Japanese Journal of Clinical Oncology*, 40(2): 153-156.

Thornton et al., "Analysis of the Sugar Specificity and Molecular Location of the β-Glucan-Binding Lectin Site of the Complement Receptor Type 3 (CD11b/CD18)", Feb. 1, 1996, *J Immunol.*, 156(3):1235-46.

Tsikitis et al., "The Lectin-Like Domain of Complement Receptor 3 Protects Endothelial Barrier Function from Activated Neutrophils", Jul. 15, 2004, *J Immunol.*, 173(2):1284-91.

Xia et al., "The β-Glucan-Binding Lectin Site of Mouse CR3 (CD11b/CD18) and Its Function in Generating a Primed State of the Receptor That Mediates Cytotoxic Activation in Response to iC3b-Opsonized Target Cells", Feb. 15, 1999, *J Immunol.*, 162(4):2281-90.

Zhong et al., "Effect of Yeast-derived β-glucan in Conjunction With Bevacizumab for the Treatment of Human Lung Adenocarcinoma in Subcutaneous and Orthotopic Xenograft Models", Sep. 2009, *Journal of Immunotherapy*, 32(7):703-712.

Kaiser et al., "Synergism between Poly-(1-6)-β-D-Glucopyranosyl-(1-3)-β-D-Glucopyranose Glucan and Cefazolin in Prophylaxis of Staphylococcal Wound Infection in a Guinea Pig Model", Sep. 1998, *Antimicrob. Agents Chemother.*, 42(9):2449-2451. Retrieved on Mar. 30, 2017. Retrieved from the Internet <http://aac.asm.org/content/42/9/2449.full.pdf+html>.

Vasilakos, et al., "Human innate immune cells that engage soluble beta-1,3/1,6 glucans: Role for complement receptor 3 (CR3, CD11b/CD18)", 2010, *J. Immunol.*, 184(1) Suppl. Abstract No. 89,53.

Fraser, Callum, "Test result variation and the quality of evidence-based clinical guidelines," *Clinica Chimica Acta*, 2004;346:19-24.

* cited by examiner

*Figure 11*

COMPOSITIONS AND METHODS FOR BETA-GLUCAN IMMUNOTHERAPY

CROSS-REFERENCE TO RELATED APPLICATION

This application is the U.S. National Stage Application of International Application No. PCT/US2013/031625, entitled COMPOSITIONS AND METHODS FOR β-GLUCAN IMMUNOTHERAPY, filed on Mar. 14, 2013, which claims priority to U.S. Provisional Patent Application Ser. No. 61/640,834, filed May 1, 2012, U.S. Provisional Patent Application Ser. No. 61/640,842, filed. May 1, 2012, and U.S. Provisional Patent Application Ser. No. 61/640,397, filed Apr. 30, 2012, each of which is incorporated herein by reference.

SUMMARY

This disclosure describes, in one aspect, a composition that includes a β-glucan component and an antibody component that specifically binds to the β-glucan. In some embodiments, the β-glucan may be derived from yeast. In some embodiments, the β-glucan can include a β-1,3/1,6 glucan such as β(1,6)-[poly-(1,3)-D-glucopyranosyl]-poly-β(1,3)-D-glucopyranose.

In some embodiments, the antibody component can include a monoclonal antibody that specifically binds to the β-glucan. In some embodiments, the monoclonal antibody can include BfD I, BfD II, BID III, or BfD IV.

In some embodiments, the β-glucan component and the antibody component can be provided in a single formulation. In other embodiments, the β-glucan component and the antibody component can be provided in separate formulations.

In another aspect, this disclosure describes a method that generally includes co-administering to a subject a β-glucan and an antibody preparation that specifically binds to the β-glucan. In some embodiments, the method can further include administering to the subject an anti-tumor antibody.

In another aspect, this disclosure describes a method of increasing a subject's response to β-glucan immunotherapy. Generally, the method includes co-administering to the subject a composition that comprises a β-glucan and an antibody preparation that specifically binds to the β-glucan. In some embodiments, the method can further include identifying the subject as a low binder and administering a composition that comprises a β-glucan and an antibody preparation that specifically binds to the β-glucan.

In some embodiments of any of these methods, the β-glucan and the antibody preparation may be co-administered simultaneously. In other embodiments of any of the methods, the antibody preparation may be co-administered at different times. In some embodiments of any of the methods, the β-glucan and the antibody preparation may be co-administered at different sites.

In some embodiments of these methods, the β-glucan may be derived from yeast. In some embodiments of these methods, the β-glucan can include a β-1,3/1,6 glucan such as β(1,6)-[poly-(1,3)-D-glucopyranosyl]-poly-β(1,3)-D-glucopyranose.

In some embodiments of these methods, the antibody component can include a monoclonal antibody that specifically binds to the β-glucan such as BID I, BID II, BID III, or BfD IV.

In another aspect, this disclosure describes a method of increasing a subject's response to β-glucan immunotherapy involving an antibody. Generally, the method includes administering to the subject a composition that includes a β-glucan moiety conjugated to the antibody. In some embodiments, the β-glucan moiety may conjugated to a therapeutic antibody such as, for example, an anti-tumor antibody. In some embodiments, the method further includes identifying the subject as a low binder of β-glucan.

In some embodiments, the β-glucan moiety may be derived from yeast. In some embodiments, the β-glucan moiety can be, or is derived from, a β-1,3/1,6 glucan such as β(1,6)-[poly-(1,3)-D-glucopyranosyl]-poly-β(1,3)-D-glucopyranose.

In some embodiments, the β-glucan therapy can include administering to a subject a β-glucan, antibody that specifically binds β-glucan, and a therapeutic antibody. In some cases, the therapeutic antibody can include an anti-tumor antibody.

The above summary of the present invention is not intended to describe each disclosed embodiment or every implementation of the present invention. The description that follows more particularly exemplifies illustrative embodiments. In several places throughout the application, guidance is provided through lists of examples, which examples can be used in various combinations. In each instance, the recited list serves only as a representative group and should not be interpreted as an exclusive list.

DETAILED DESCRIPTION OF ILLUSTRATIVE EMBODIMENTS

This disclosure describes methods related to the use of β-glucan as a component of immunotherapy. The compositions and methods described herein exploit the observation of differential binding of β-glucan by immune cells in different populations of healthy humans. Surprisingly, "high binders" of β-glucan exhibit higher titers of anti-β-glucan antibodies than "low binders." Thus, this disclosure describes compositions that include a β-glucan component and an antibody component that specifically binds to the β-glucan. This disclosure also describes methods that generally include co-administering a β-glucan and an antibody or antibody component that specifically binds the β-glucan, or a β-glucan moiety conjugated to an antibody or antibody fragment. Such methods can convert a "low binder" to a "high binder" and, thus, increase the population for whom β-glucan-based immunotherapy can be effective.

β-glucans are polymers of glucose derived from a variety of microbiological and plant sources including, for example, yeast, bacteria, algae, seaweed, mushroom, oats, and barley. Of these, yeast β-glucans have been extensively evaluated for their immunomodulatory properties. Yeast β-glucans can be present as various forms such as, for example, intact yeast, zymosan, purified whole glucan particles, solubilized zymosan polysaccharide, or highly-purified soluble β-glucans of different molecular weights. Structurally, yeast β-glucans are composed of glucose monomers organized as a β-(1,3)-linked glucopyranose backbone with periodic β-(1,3) glucopyranose branches linked to the backbone via β-(1,6) glycosidic linkages. The different forms of yeast β-glucans can function differently from one another. The mechanism through which yeast β-glucans exert their immunomodulatory effects can be influenced by the structural differences between different forms of the β-glucans such as, for example, its particulate or soluble nature, tertiary conformation, length of the main chain, length of the side chain, and frequency of the side chains. The immune stimulating functions of yeast β-glucans are also dependent upon the receptors engaged in different cell types in different species, which again, is dependent on the structural properties of the β-glucans.

In one aspect, this disclosure describes a composition that includes, generally, a β-glucan component and an antibody component that specifically binds to the β-glucan.

The β-glucan component may include any suitable form of β-glucan or any combination of two or more forms of β-glucan. Suitable β-glucans and the preparation of suitable β-glucans from their natural sources are described in, for example, U.S. Patent Application Publication No. US2008/0103112 A1. In some embodiments, the β-glucan may be derived from a yeast such as, for example, *Saccharomyces cerevisiae*. In certain specific embodiments, the β-glucan may be or be derived from β(1,6)-[poly-(1,3)-D-glucopyranosyl]-poly-β(1,3)-D-glucopyranose, also referred to herein as PGG (IMPRIME PGG, Biothera, Inc., Eagan, Minn.), a highly purified and well characterized form of yeast-derived β-glucan. Thus, the β-glucan component can include, for example, a modified and/or derivatized β-glucan such as those described in International Patent Application No. PCT/US12/36795. In other embodiments, the β-glucan component can include, for example, a particulate-soluble β-glucan or a particulate-soluble β-glucan preparation, each of which is described in, for example, U.S. Pat. No. 7,981,447.

The antibody component of the composition can include any antibody preparation that specifically binds to the β-glucan component of the composition. As used herein, "specific" and variations thereof refer to having a differential or a non-general (i.e., non-specific) affinity, to any degree, for a particular target. Thus, the antibody component can include a polyclonal antibody preparation (e.g., derived from serum), a monoclonal antibody preparation, or any antibody fragment such as an Fc portion. Exemplary monoclonal antibodies that specifically bind β-glucan include, for example, monoclonal antibodies identified as BfD I, BfD II, BfD III, and/or BID IV (Biothera, Inc., Eagan, Minn.), each of which is described in U.S. Pat. No. 6,294,321.

The antibody or antibody fragment (e.g., the Fc portion) conjugated to the β-glucan component can be any suitable antibody or antibody fragment that can be linked to the β-glucan component.

The β-glucan component, the antibody component, and/or the combination of both components may be formulated in a composition along with a "carrier." As used herein, "carrier" includes any solvent, dispersion medium, vehicle, coating, diluent, antibacterial agent and/or antifungal agent, isotonic agent, absorption delaying agent, buffer, carrier solution, suspension, colloid, and the like. The use of such media and/or agents for pharmaceutical active substances is well known in the art. Except insofar as any conventional media or agent is incompatible with the β-glucan or the antibody, its use in the therapeutic compositions is contemplated. Supplementary active ingredients also can be incorporated into the compositions.

By "pharmaceutically acceptable" is meant a material that is not biologically or otherwise undesirable, i.e., the material may be administered to an individual along with the β-glucan and/or the antibody without causing any undesirable biological effects or interacting in a deleterious manner with any of the other components of the pharmaceutical composition in which it is contained.

The β-glucan component, the antibody component, and/or the combination of both components may be formulated into a pharmaceutical composition. In some embodiments, the β-glucan component of the composition and the antibody component of the composition may be provided in a single formulation. In other embodiments, the β-glucan component and the antibody component may be provided in separate formulations. The composition may be formulated in a variety of and/or a plurality of forms adapted to one or more preferred routes of administration. Thus, a composition can be administered via one or more known routes including, for example, oral, parenteral (e.g., intradermal, transcutaneous, subcutaneous, intramuscular, intravenous, intraperitoneal, etc.), or topical (e.g., intranasal, intrapulmonary, intramammary, intravaginal, intrauterine, intradermal, transcutaneous, rectally, etc.). A composition, or a portion thereof, can be administered to a mucosal surface, such as by administration to, for example, the nasal or respiratory mucosa (e.g., by spray or aerosol). A composition, or a portion thereof, also can be administered via a sustained or delayed release.

A formulation may be conveniently presented in unit dosage form and may be prepared by methods well known in the art of pharmacy. Methods of preparing a composition with a pharmaceutically acceptable carrier include the step of bringing the β-glucan and/or the antibody into association with a carrier that constitutes one or more accessory ingredients. In general, a formulation may be prepared by uniformly and/or intimately bringing the active compound into association with a liquid carrier, a finely divided solid carrier, or both, and then, if necessary, shaping the product into the desired formulations.

The β-glucan component, the antibody component, and/or the combination of both components may be provided in any suitable form including but not limited to a solution, a suspension, an emulsion, a spray, an aerosol, or any form of mixture. The composition may be delivered in formulation with any pharmaceutically acceptable excipient, carrier, or vehicle. For example, the formulation may be delivered in a conventional topical dosage form such as, for example, a cream, an ointment, an aerosol formulation, a non-aerosol spray, a gel, a lotion, and the like. The formulation may further include one or more additives including such as, for example, an adjuvant, a skin penetration enhancer, a colorant, a fragrance, a flavoring, a moisturizer, a thickener, and the like.

In another aspect, the invention provides a method that generally includes co-administering to a subject, in effective amounts with one another, a β-glucan and an antibody preparation that specifically binds the β-glucan. As used herein, "co-administered" refers to two or more components of a combination administered so that the therapeutic or prophylactic effects of the combination can be greater than the therapeutic or prophylactic effects of either component administered alone. Two components may be co-administered simultaneously or sequentially. Simultaneously co-administered components may be provided in one or more pharmaceutical compositions. Sequential co-administration of two or more components includes cases in which the components are administered so that both components are simultaneously bioavailable after both are administered. Regardless of whether the components are co-administered simultaneously or sequentially, the components may be co-administered at a single site or at different sites. Also as used herein, "an effective amount" refers to the amount of β-glucan and antibody that specifically binds to the β-glucan effective to increase binding of the β-glucan to immune cells—e.g., polymorphonuclear leukocytes (PMNs), monocytes, or neutrophils—or to increase production of cytokines and/or chemokines associated with binding of β-glucans—e.g., IL-8 production.

β-glucans suitable for use in the methods include one or more of those described as suitable for use as the β-glucan component of the compositions described above. Also, the antibody preparation can include one or more antibodies described as suitable for use as the antibody component of the compositions described above.

The amount of β-glucan and antibody effective to induce one or more of the desired effects can vary depending on various factors including, but not limited to, the weight, physical condition, and/or age of the subject, and/or the route of administration. Thus, the absolute amount of β-glucan and antibody that specifically binds the β-glucan that are included in a given unit dosage form can vary widely, and depends upon factors such as the species, age, weight and physical condition of the subject, as well as the method of administration. Accordingly, it is not practical to set forth generally the amount that constitutes an amount of β-glucan and antibody effective for all possible applications. Those of ordinary skill in the art, however, can readily determine the appropriate amount with due consideration of such factors.

In some embodiments, the method can include administering sufficient β-glucan to provide a dose of, for example, from about 100 ng/kg to about 50 mg/kg to the subject, although in some embodiments the methods may be performed by administering the β-glucan in a dose outside this range. In some embodiments, the method includes administering sufficient β-glucan to provide a dose of from about 10 µg/kg to about 10 mg/kg to the subject such as, for example, a dose of about 1 mg/kg, about 2 mg/kg, about 3 mg/kg, about 4 mg/kg, about 5 mg/kg, about 6 mg/kg, about 7 mg/kg, about 8 mg/kg, about 9 mg/kg, or about 10 mg/kg. In one particular embodiment, the method includes administering sufficient β-glucan to provide a dose of 4 mg/kg.

Alternatively, the dose may be calculated using actual body weight obtained just prior to the beginning of a treatment course. For the dosages calculated in this way, body surface area (m$^2$) is calculated prior to the beginning of the treatment course using the Dubois method: m$^2$=(wt kg$^{0.425}$×height cm$^{0.725}$)×0.007184. In some embodiments, therefore, the method can include administering sufficient β-glucan to provide a dose of, for example, from about 0.01 mg/m$^2$ to about 10 mg/m$^2$.

In some embodiments, the method can include administering sufficient antibody that specifically binds the β-glucan to provide a dose of, for example, from about 100 ng/kg to about 50 mg/kg to the subject, although in some embodiments the methods may be performed by administering the antibody in a dose outside this range. In some embodiments, the method includes administering sufficient antibody to provide a dose of from about 10 µg/kg to about 5 mg/kg to the subject, for example, a dose of from about 100 µg/kg to about 1 mg/kg. In some embodiments, antibody that specifically binds the β-glucan can be administered in the form of intravenous immunoglobulin (WIG), a blood product that contains pooled polyvalent IgG from many donors (typically many hundreds, even thousands, of donors and, thus, naturally containing anti-β-glucan antibodies). In such embodiments, IVIG may be administered in a dose of from about 0.1 g/kg to about 2.0 g/kg such as, for example, 0.1 g/kg, 0.2 g/kg, 0.3 g/kg, 0.4 g/kg, 0.5 g/kg, 0.6 g/kg, 0.7 g/kg, 0.8 g/kg, 0.9 g/kg, 1.0 g/kg, 1.1 g/kg, 1.2 g/kg, 1.3 g/kg, 1.4 g/kg, 1.5 g/kg, 1.6 g/kg, 1.7 g/kg, 1.8 g/kg, 1.9 g/kg, or 2.0 g/kg. In certain embodiments, IVIG may be administered to provide a dose of about 0.4 g/kg to about 1.0 g/kg.

Alternatively, the dose may be calculated using actual body weight obtained just prior to the beginning of a treatment course. For the dosages calculated in this way, body surface area (m$^2$) is calculated prior to the beginning of the treatment course using the Dubois method: m$^2$=(wt kg$^{0.425}$×height cm$^{0.325}$)×0.007184. In some embodiments, therefore, the method can include administering sufficient antibody to provide a dose of, for example, from about 0.01 mg/m$^2$ to about 10 mg/m$^2$.

In some embodiments, the β-glucan and antibody may be co-administered, for example, from a single dose to multiple doses per week, although in some embodiments the method may be performed by co-administering the β-glucan and antibody at a frequency outside this range. In certain embodiments, the β-glucan and antibody may be administered from about once per year to once per week.

Figure 1:
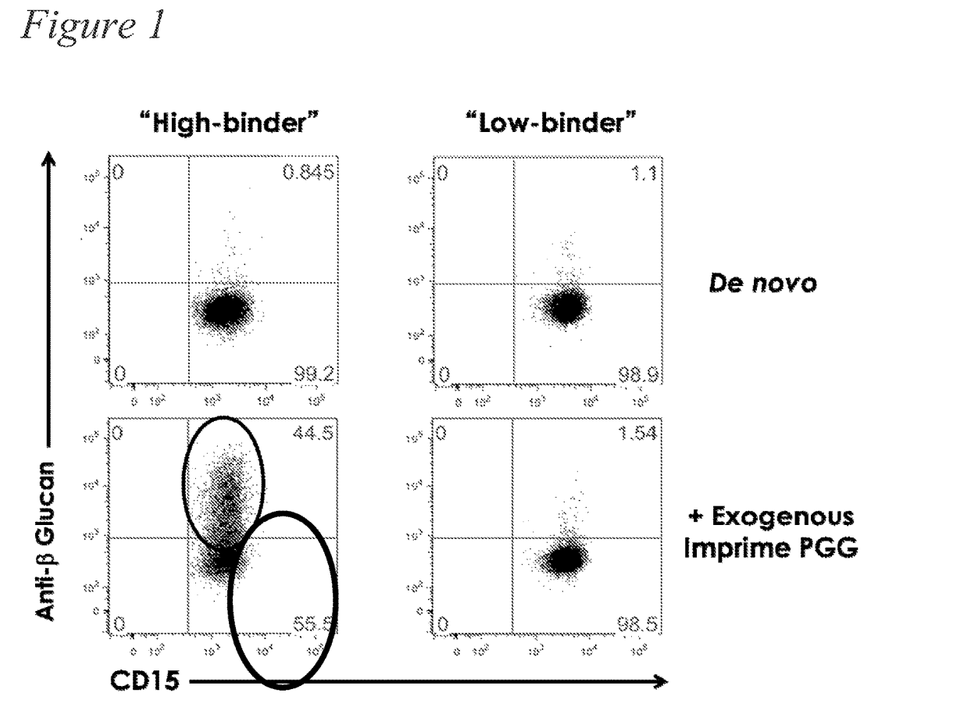
FIG. 1. Flow cytometry data showing differential β-glucan (PGG) binding to polymorphonuclear leukocytes in healthy human whole blood.
Figure 2:
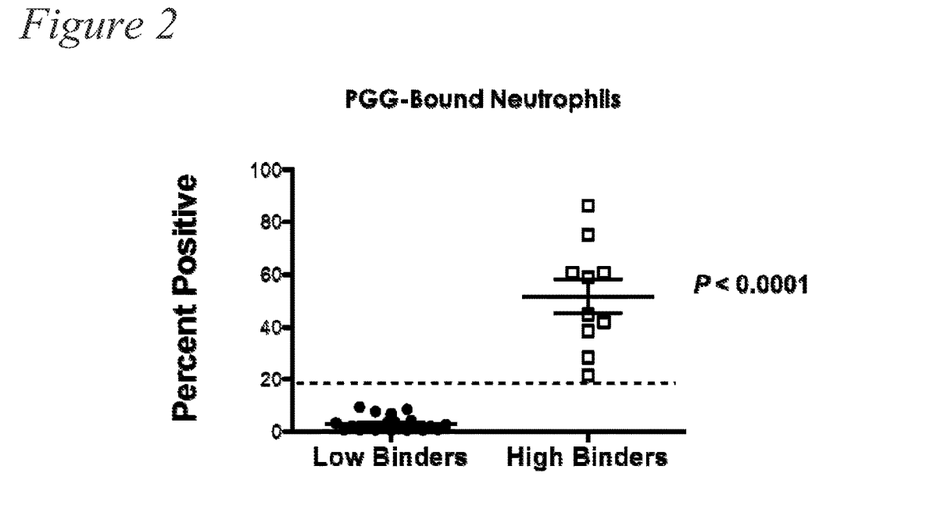
FIG. 2. Data showing differential β-glucan binding to neutrophils in healthy human whole blood.
Figure 3:
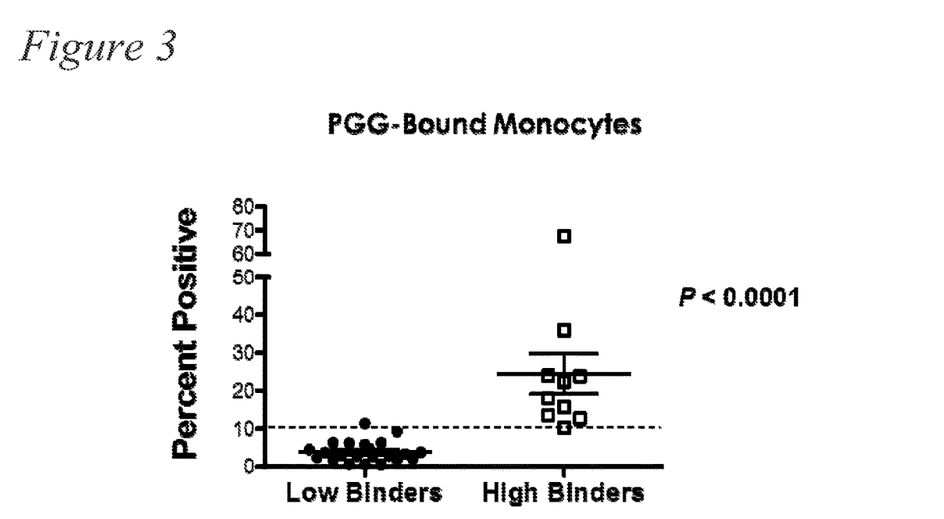
FIG. 3. Data showing differential β-glucan binding to monocytes in healthy human whole blood.

As noted above, yeast β-glucans have been extensively evaluated for their immunomodulatory properties. We discovered, however, that distinct populations of individuals exist: one population exhibits relatively high capacity of β-glucan binding to innate immune cells in whole blood; another population exhibits relatively low capacity of β-glucan binding to innate immune cells in whole blood. This observation was wholly unexpected based on data from mouse models of immunity and studies involving isolated human immune cells. Many individuals exhibit some level of β-glucan binding to immune cells from native, low level exposure to β-glucans. (e.g., FIG. 1, "De novo"). When exogenous β-glucan is administered, "low binders" exhibit a modest increase in the percentage of innate immune cells that bind β-glucan, while "high binders" exhibit a marked increase in the percentage of innate immune cells that bind β-glucan. (FIG. 1., "+Exogenous PGG"). FIG. 1 and FIG. 2 show data reflecting β-glucan binding to polymorphonuclear leukocytes (PMNs), and FIG. 3 (monocytes) shows that the differential binding applies to other immune cell populations as well. In addition, "high binders" also tend to produce more cytokines and/or chemokines such as, for example, IL-8, MCP, MIP-1, etc.

As used herein, status as a "high binder" refers to an individuals who exhibit a predetermined percentage of a particular immune cell population that binds exogenously provided β-glucan. The immune cell population used to determine whether an individual is a "high binder" or a "low binder" can be, for example, polymorphonuclear lymphocytes (PMNs) or monocytes. An individual can be considered a "high binder" if at least 10% of the PMNs or monocytes in a blood sample from the individual bind exogenously provided β-glucan. Thus, an individual may be a "high binder" if at least 10%, at least 12%, at least 15%, at least 20%, at least 15%, or at least 40% of PMNs or monocytes in a blood sample from the individual bind exogenously provided β-glucan. (See, e.g., FIG. 2 and FIG. 3). In some cases, the exogenously provided β-glucan can include PGG provided to final concentration of 10 µg/mL to 100 µg/mL. Status as a "low binder" refers to an individual who fails to exhibit "high binder" status.

Figure 4:
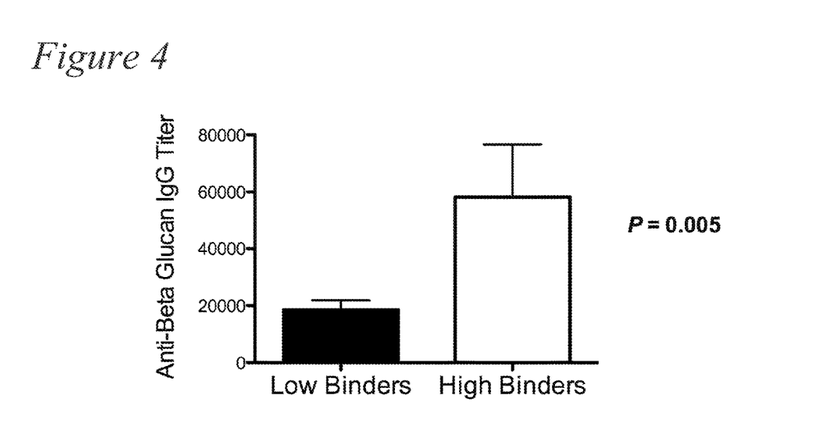
FIG. 4. Data comparing anti-β-glucan antibody titers of low binders and high binders.

Moreover, "high binders" can exhibit higher titers of anti-β-glucan antibodies than "low binders." (FIG. 4). A typical anti-β-glucan antibody titer for a "high binder" can be a titer of at least 25,000 such as, for example, at least 30,000, at least 35,000, at least 40,000, at least 45,000, at least 50,000, at least 55,000, or at least 60,000. (See, e.g., FIG. 4). Anti-β-glucan antibody titers typically refers to IgG. In some cases, however, the presence of IgM can compensate for a lower IgG titer to help establish "high binder" status.

β-glucans are known to bind a lectin-like domain within the COOH-terminal region of the CD11b subunit of leukocyte complement receptor 3 (CR3; CD11b/CD18, aMh2 integrin, Mac-1; refs. Thorton et al., *J Immunol* 156:1235-46, Xia et al., *J Immunol* 162:2281-90). β-glucans can prime CR3 of neutrophils, macrophages, and natural killer cells for cytotoxicity against tumors opsonized with iC3b. Dual occupancy of leukocyte CR3 by the I-domain ligand iC3b and the lectin-like domain ligand β-glucan can lead to degranulation and cytotoxic responses (Li et al., *J Immunol* 177:1661-9; Tsikitis et al., *J Immunol* 173:1284-91). Thus, one might suspect that "low binder" individuals might possess higher natural titers of anti-β-glucan antibodies that can disrupt binding between β-glucan and CR3.

We found, however, exactly the opposite. "High binders" exhibited higher titers of anti-β-glucan antibodies than "low binders." (FIG. 4). Thus, higher titers of anti-β-glucan antibodies are associated with enhanced β-glucan binding to CR3 on immune cells.

Figure 5:
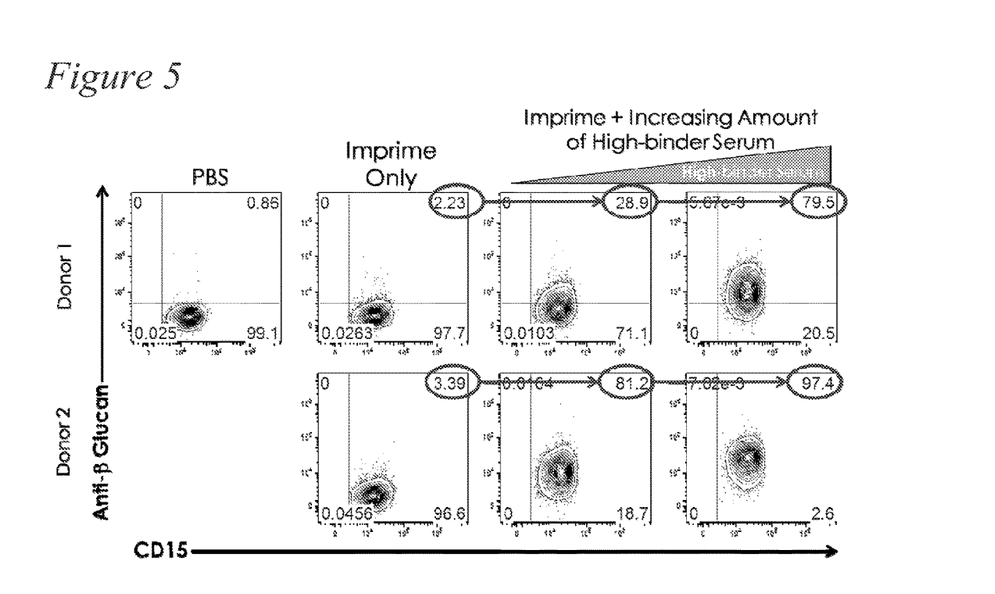
FIG. 5. Data showing that high binder serum can increase β-glucan binding to PMNs obtained from a low binder.
Figure 6:
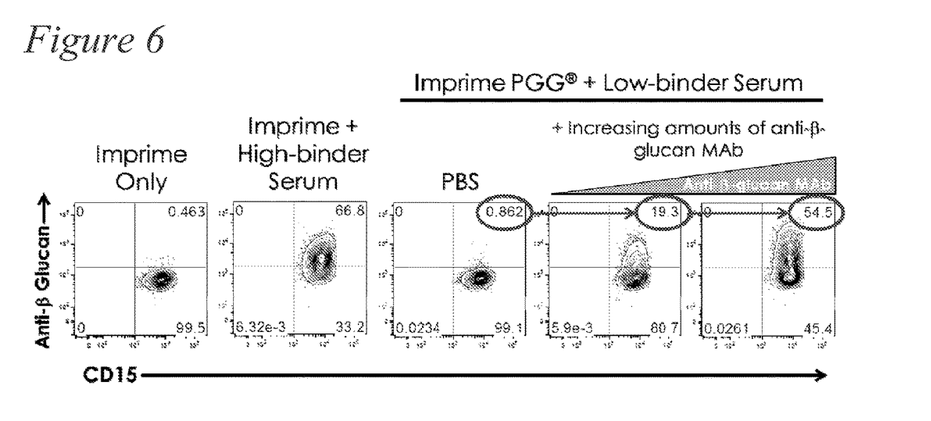
FIG. 6. Data showing the anti-β-glucan antibodies can increase β-glucan binding to PMNs from a low binder.
Figure 7:
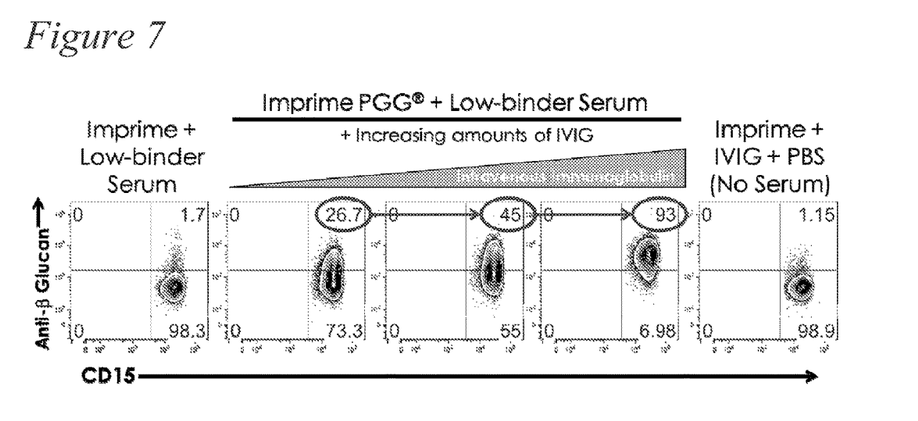
FIG. 7. Data showing intravenous immunoglobulin can increase β-glucan binding to PMNs from a low binder.

Moreover, the effect is transferable. "High binder" serum can increase β-glucan binding to immune cells (e.g., PMNs) of a "low binder." (FIG. 5). Increasing amounts of anti-β-glucan monoclonal antibody also can increase β-glucan binding to immune cells (e.g., PMNs) in serum from a "low binder." (FIG. 6). Also, intravenous immunoglobulin, a blood product that contains pooled, polyvalent IgG from many donors (typically many hundreds, even thousands, of donors) and high natural anti-β-glucan titers, also can increase β-glucan binding to immune cells (e.g., PMNs) in serum from a "low binder." (FIG. 7).

Figure 8:
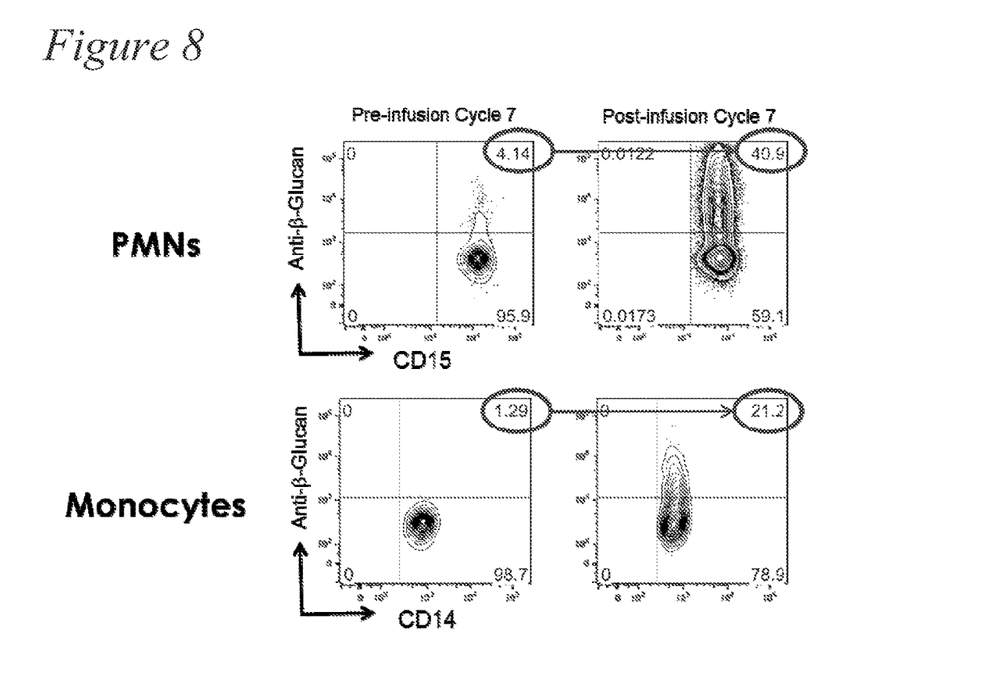
FIG. 8. Data showing conversion of a low binder to a high binder by treatment with intravenous immunoglobulin that includes a combination of β-glucan and anti-β-glucan antibodies.

The effect also is demonstrable in vivo. A subject with recurrent metastatic colorectal cancer exhibited as a "low binder" over five cycles of therapy that included administration of β-glucan. The subject exhibited β-glucan binding to <5% of PMNs and monocytes and an anti-β-glucan antibody titer in the bottom 10% of the distribution curve for healthy individuals (1:1,600 to 1:3,200). The subject was treated multiple times with intravenous immunoglobulin (IVIG) (0.4 g/kg-1 g/kg). Pre- and post-treatment samples were obtained before and after the second treatment. FIG. 8 shows that the subject exhibited a low capacity to bind β-glucan in PMNs and monocytes in the pre-treatment samples (FIG. 8, Pre-infusion Cycle 7), but had a significant increase in the capacity to bind β-glucan in post-IVIG treatment samples (FIG. 8, Post-infusion Cycle 7). In the post-treatment sample, the subject's titer of anti-β-glucan antibodies also increased to 1:25,600, demonstrating the transfer of anti-β-glucan antibodies with the IVIG treatment.

Figure 9:
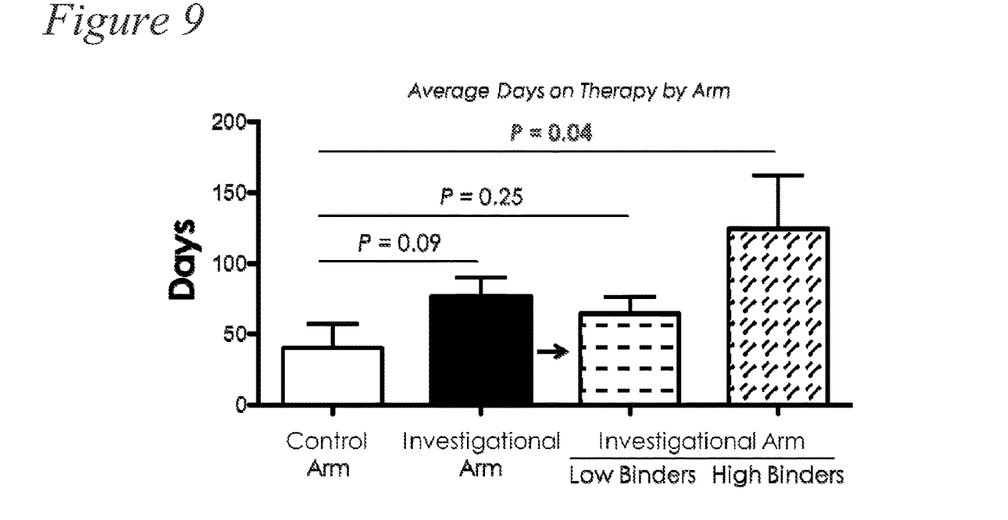
FIG. 9. Comparison of the average number of days on therapy for patients in control and investigational arms of two-armed, open-label, randomized, multi-center study.

In addition, in a two-armed, open-label, randomized, multi-center study, 795 subjects with recurrent/progressive colorectal cancer after at least two previous chemotherapeutic treatments were divided into a control arm and an investigational arm. Subjects in the control arm received treatment with cetuximab. Subjects in the investigational arm received treatment with cetuximab+4 mg/kg PGG β-glucan. FIG. 9 shows that while subjects receiving β-glucan as part of their immunotherapy remained on therapy for a longer average period than subjects receiving only cetuximab, the effect was greatest in those subjects that were "high binders." In this context, length of therapy is an indication of therapy success so that a longer therapy time indicates a positive therapeutic outcome while a shorter length of therapy indicates poorer outcomes. Thus, there is a clinical consequence to "high binder" status versus "low binder" status.

Thus, in another aspect, this disclosure describes immunotherapy that includes administering to a subject β-glucan co-administered with antibody that specifically binds β-glucan and, in addition, an anti-tumor antibody. As used herein, "anti-tumor" antibody refers to an antibody that specifically binds neoplastic cells, regardless of whether the neoplastic cells form a solid tumor or include leukemic or lymphomic cells. The β-glucan and antibody that specifically binds the β-glucan may be administered as described in detail above. The anti-tumor antibody may be any suitable anti-tumor antibody administered as directed by the manufacturer or health professional. In this context, co-administering the β-glucan and the antibody preparation can increase the efficacy of the immunotherapy. For example, PGG β-glucan has demonstrated preclinical activity against a variety of cancer types when administered in combination with anti-tumor monoclonal antibodies (mAbs). Exemplary types of cancer and their associated anti-tumor mAbs include, for example, T-cell lymphoma (anti-MUC1, anti-GD2), non-Hodgkin's lymphoma (rituximab), chronic lymphocytic leukemia (rituximab), lung carcinoma (anti-MUC1), breast adenocarcinoma (anti-MMTV), ovarian carcinoma (bevacizumab), non-small-cell lung carcinoma (bevacizumab, cetuximab), colorectal cancer (cetuximab), and pancreatic carcinoma (cetuximab, anti-MUC1). For some subjects, the immunostimulatory effect of PGG β-glucan may be enhanced by co-administering antibody that specifically binds the β-glucan.

Figure 10:
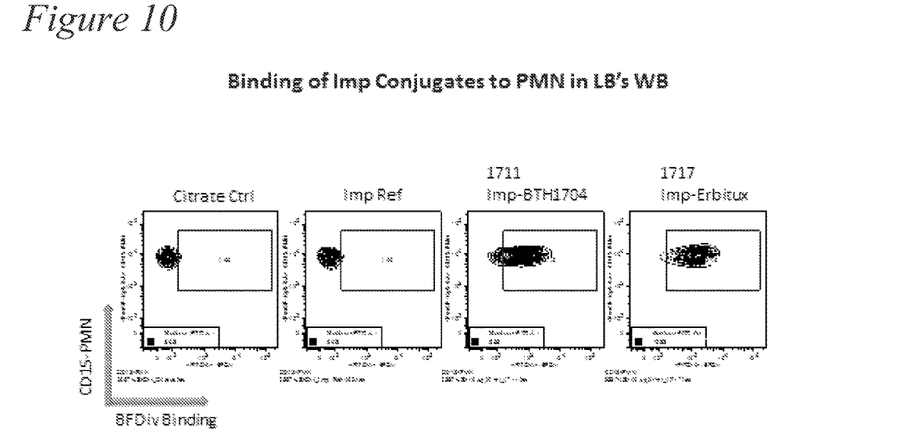
FIG. 10. Data showing binding of PGG-antibody conjugates to PMNs.
Figure 11:
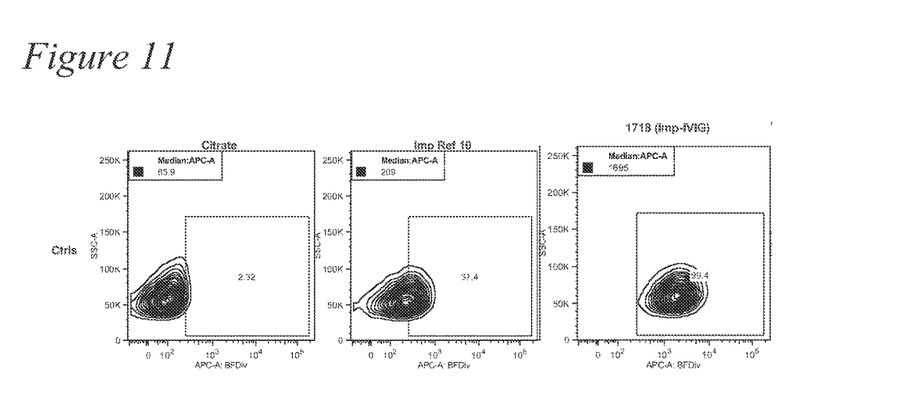
FIG. 11. Data showing binding of PGG-IVIG conjugates to PMNs.

A similar conversion of status from "low binder" to "high binder" can occur by administering to the subject a composition that includes a β-glucan moiety conjugated to any antibody or a portion of an antibody. FIG. 10 shows data illustrating relatively low PGG binding by PMNs in whole blood (Imp Ref, second panel) changing to high binding status by conjugating the PGG to either BTH1704 (anti-MUC1, U.S. Pat. No. 6,204,366, Biothera, Inc., Eagan, Minn., third panel) or ERBITUX (Eli Lilly and Co., Indianapolis, Tenn., fourth panel) anti-tumor antibodies. FIG. 11 also illustrates relatively low PGG binding by PMNs in whole blood (Imp Ref, second panel) changing to high binding status by conjugating the PGG to intravenous immunoglobulin (IVIG, Biolegend, San Diego, Calif.). Thus, in another aspect, this disclosure describes immunotherapy that includes administering to a subject a composition that includes a β-glucan moiety conjugated to an antibody, a therapeutic antibody, an anti-tumor antibody, or an antibody fragment such as the Fc portion of an antibody. Modified and/or derivatized PGG, including PGG conjugates of a PGG moiety and an antibody are described in International Patent Application No. PCT/US12/36795, which may also be applied to conjugates of antibody fragments. The PGG moiety may be, or be derived from a β-1,3/1,6 glucan. In this context, "derived from" acknowledges that a conjugate may necessarily be prepared by creating a covalent linkage that replaces one or more atoms of the PGG β-glucan. As used herein, "derived from a β-1,3/1,6 glucan" refers to a portion of the PGG β-glucan that remains as part of a conjugate after replacing one or more atoms of the PGG to form the covalent linkage of the conjugate.

The therapeutic antibody may be any therapeutic antibody capable of being combined with β-glucan for immunotherapy. Thus, the therapeutic antibody also can include any of the anti-tumor antibodies described above in connection with other aspects of this disclosure in order to provide immunotherapy against various forms of cancer.

As used herein, the term "and/or" means one or all of the listed elements or a combination of any two or more of the listed elements; the terms "comprises" and variations thereof do not have a limiting meaning where these terms appear in the description and claims; unless otherwise specified, "a," "an," "the," and "at least one" are used interchangeably and mean one or more than one; and the recitations of numerical ranges by endpoints include all numbers subsumed within that range (e.g., 1 to 5 includes 1, 1.5, 2, 2.75, 3, 3.80, 4, 5, etc.).

In the preceding description, particular embodiments may be described in isolation for clarity. Unless otherwise expressly specified that the features of a particular embodiment are incompatible with the features of another embodiment, certain embodiments can include a combination of compatible features described herein in connection with one or more embodiments.

For any method disclosed herein that includes discrete steps, the steps may be conducted in any feasible order. And, as appropriate, any combination of two or more steps may be conducted simultaneously.

The present invention is illustrated by the following examples. It is to be understood that the particular examples, materials, amounts, and procedures are to be interpreted broadly in accordance with the scope and spirit of the invention as set forth herein.

EXAMPLES

Example 1

Materials

Imprime PGG (Biothera, Inc., Eagan, Minn.) was provided as a preservative-free, soluble β-glucan formulation prepared at a concentration of 1 mg/mL in 0.8% sodium chloride and 0.2% sodium citrate monobasic, at a pH of 6.4. The compound was stored at 4-8° C. until use.

Preparation of Samples

Whole Blood.

Fresh whole blood (WB) was obtained from healthy volunteers that had provided informed consent prior to donation (New England Institutional Review Board, May 2007). The blood was collected in a Vacutainer® containing 158 USP Units Freeze-Dried Sodium Heparin (BD Biosciences; San Jose, Calif.).

Serum and Plasma.

Whole blood was processed into serum or plasma by Vacutainer® tubes (BD Biosciences; San Jose, Calif.) collection with either serum separator (red top) or sodium heparin (green top) tubes. Tubes were mixed well, incubated at room temperature for 30 minutes, and then centrifuged at 2000 rpm (1150×g) for 10 minutes. The supernatant (either serum or plasma) was then transferred to a fresh polycarbonate storage conical tube.

Anti-BG ELISA Method

A preliminary ELISA method modified from the monkey anti-β-glucan method (Noss et al., 2012 *Int. Arch. Allergy Immunol.*, 157:98-108) was used to test the human sera samples. Costar universal binding plates were coated with 50 μL of β-glucan at 1 μg/mL purified β-glucan diluted in purified water and incubated at 37° C. for 30 minutes. The coated plate was then exposed to high intensity ultraviolet light at >1500 μW/cm$^2$ for five minutes at room temperature and placed in a 50° C. forced air oven until dry before a second exposure to ultraviolet light at >1500 μW/cm$^2$ for five minutes at room temperature. The plate was then blocked with a 0.5% solution of Bovine Serum Albumin for >30 minutes before washing with wash buffer (phosphate buffered saline [PBS] with 0.05% Tween-20). Human serum samples were diluted into wash buffer added to the plate and subsequently serially diluted in wash buffer on the plate. Test samples diluted 1:400 were pipetted onto the test plate with seven additional serial 1:2 dilutions (serum dilutions between 1:400 and 1:12,800). Samples were incubated at room temperature for 30 minutes to permit human IgG to bind to the plate-bound β-glucan antigen. Following incubation the wells were washed with wash buffer and an enzyme labeled secondary antibody (horseradish peroxidase conjugated affinity purified goat anti human IgG, Fc gamma specific) was incubated in the wells to bind with the human IgG bound to the β-glucan antigen. The secondary antibody was allowed to incubate for 30 minutes before washing with wash buffer. After the entire wash buffer was removed from the wells a peroxidase substrate was incubated in the wells and color development was quenched with 1 M phosphoric acid at five minutes color development. The optical density (OD) at 450 nm was measured using a microtiter plate reader.

Determining Anti-β-Glucan Ab Titer

Resulting OD from replicate wells were averaged and the mean assay background subtracted. The greatest dilution giving a background adjusted OD greater than or equal to 0.100 was considered the samples titer and was expressed as the inverse of that dilution. For definition of assay performance a value was assigned the standard reference serum and a reference curve was constructed on each assay plate. For example a test sample giving a background adjusted OD of 0.100 at a dilution of 1:12,800 was considered to have a titer of 12,800. Where samples were tested multiple times and the average of their titers fell between the serial 1:2 titer levels from 1:400 the next lowest titer level was reported as its titer. For example, one donor's serum from four donations was tested in five separate assays resulting in a mean titer of 28,160; its titer was reported to be 25,600.

Assay Standard Curve.

A value of 160 Arbitrary Units per mL (AU/mL) was assigned to the standard human anti-β-glucan antibody. Thus a 1:400 dilution in the assay method results in a value of 400 mAU/mL as the highest point of a standard dilution curve additional serial 1:2 dilutions were prepared on the assay plate. Assay controls were diluted 1:100 in ELISA wash buffer for testing. Furthermore two dilutions of each control level were independently prepared for testing on each plate in parallel.

Statistical Analysis.

Plotting standard concentration in mAU/mL versus mean background corrected optical density resulted in a standard reference curve. Using the ELISA software a 4-parameter fit was computed from the standard dose response curve to determine unknown values for samples, controls and test serum. Assay response values falling between the upper and lower inflection points of the standard curve (linear portion) were used to determine a samples test value. To compute the coefficient of variation (% CV); the standard deviation of a set of values was divided by the mean of the same set of values and the result multiplied by 100.

Binding of PGG to Cells of Whole Blood (WB)

One hundred microliters of WB from healthy donors was aliquoted into 5 mL polystyrene fluorescence activated cell sorter (FACS) tubes. These WB samples were stimulated with either Imprime PGG (10 µg/mL or 100 µg/mL) or citrate buffer, the vehicle control. The FACS tubes containing the samples were loosely covered with the corresponding caps and incubated for 30 minutes or two hours, at 37° C. in a humidified incubator (5% $CO_2$).

TABLE 1

Antibody Cocktail Used To Stain Whole Blood Samples

| Antibody | Company; Clone # | Dilution or Final Concentration | For identification of: |
|---|---|---|---|
| Anti-CD15 | Biolegend; W6D3 | 0.2 µg/mL | neutrophils |
| Anti-CD19 | Biolegend; HIB19 | 0.63 µg/mL | B cells |
| Anti-CD14 | Biolegend; HCD14 | 5 µg/mL | monocytes |
| Anti-CD14 | Invitrogen; TüK4 | 1:50 | monocytes |
| Anti-CD3 | Biolegend; HIT3a | 0.25 µg/mL | T cells |
| Anti-CD45 | Biolegend; HI30 | 0.25 µg/mL | hematopoietic cells excluding erythrocytes and platelets |
| Goat F(ab')2 anti-mouse IgM | Jackson Immunolab | 5 µg/mL | mouse anti-β glucan antibody |

Proceeding incubation with the anti-β-glucan antibody BfD IV, the cells were incubated with the antibody cocktail which contains a secondary antibody for the recognition of BfD IV as well as antibodies for the recognition of various cell surface markers After incubation, all samples were washed by adding 2 mL of 1× Dulbecco's phosphate buffered saline (DPBS) and centrifuged at 1500-1700 rpm at 4° C. for five minutes. After two rounds of washes and aspirations, 5 µL of the anti-β-glucan antibody BfD IV (~100 µg/mL), was mixed into each tube and incubated at room temperature for 30 minutes. This primary antibody was washed off twice with 1×DPBS as described above and a cocktail of antibodies containing the secondary antibody as well as the specific cell surface markers (Table 1) was added and incubated for 30 minutes at room temperature in the dark. To lyse the red blood cells, 2 mL of 1× BD lysing solution (BD Biosciences; San Jose, Calif.) was added to each sample and gently vortexed. After an incubation period of one hour at room temperature, the samples were centrifuged at 1500-1700 rpm at 4° C. for five minutes. The BD lysing solution was aspirated and the cells were washed once with 1×DPBS and aspirated as described above. For fixation, 300-400 µL of 1% paraformaldehyde was added to each sample. The samples were acquired on the LSR II (BD Biosciences; San Jose, Calif.) within 20 hours of fixation. Data was analyzed using FlowJo software (Tree Star, Ashland, Oreg.).

Example 2

Materials

Imprime PGG (Biothera, Inc., Eagan, Minn.) was provided in a preservative-free, soluble β-glucan formulation prepared at a concentration of 1 mg/mL in 0.8% sodium chloride and 0.2% sodium citrate monobasic, at a pH of 6.4. The compound was stored at 4-8° C. until use.

Whole Blood (WB) Binding Assay

Fresh WB was obtained from healthy volunteers that had provided informed consent prior to donation (New England Institutional Review Board. Blood Donation Protocol No. 07-124). The blood was collected in a Vacutainer® containing 158 USP Units Freeze-Dried Sodium Heparin (BD Biosciences; San Jose, Calif.). Serum was collected in a Vacutainer® containing a thrombin-based clot activator (BD Biosciences; San Jose, Calif.). Approximately 20 minutes after collection, the vial was centrifuged at 2000 rpm for 10 minutes at room temperature. Serum was harvested from this vial and stored at 4° C. for use within 8 hours or at −80° C. for use after 8 hours.

The whole blood binding assay was performed by incubating whole blood samples with Imprime PGG for 30 minutes or two hours at 37° C. in a humidified incubator. After washing with 1× Dulbecco's phosphate buffered saline (DPBS), BfDIV, a mouse anti-β-glucan antibody was added and incubated with the WB for 30 minutes at room temperature. After more rounds of washing, an antibody cocktail including a goat anti-mouse detection antibody and antibodies to surface molecules were added and incubated at room temperature in the dark for 30 minutes. Erythrocytes were lysed with BD Lyse and samples were resuspended in 1% paraformaldehyde. Samples were acquired on a flow cytometer and analyzed using FlowJo software (Ashland, Oreg.).

WB and Serum Crossover Studies

For serum crossover studies, whole blood was spun down at 1200 rpm for 10 minutes and plasma removed. Blood cells were washed 1-2 times with 1×DPBS to remove remaining plasma. 50 µL of serum was added and mixed before addition of Imprime.

For incubation with anti-β-glucan IgG (BioSupplies, Australia), the lyophilized antibody was resuspended to 1 mg/mL with 1×DPBS and stored at −80° C. or 4° C. as a stock solution. Before being added to blood samples, the stock was diluted 1:10 to 100 µg/mL and 10 µL, of this solution was added to 100 µL of blood. For incubation with IVIG, 10% IVIG (100 mg/mL) (PRIVIGEN, CSL Behrling, King of Prussia, Pa.) was added to the whole blood sample at the indicated final concentrations.

Example 3

Fresh whole blood was obtained from healthy volunteers that had provided informed consent prior to donation. The blood was collected in a Vacutainer® containing 158 USP Units Freeze-Dried Sodium Heparin (BD Biosciences; San Jose, Calif.). 100 µL of whole blood from the healthy donors was aliquoted into 5 mL polystyrene FACS tubes. The samples were stimulated with either the vehicle control, or PGG reference standard, or PGG-Muc1 conjugate (Imp-BTH1704), PGG-Erbitux conjugate (10 µg/mL), or PGG-IVIG conjugate. PGG-anti-tumor antibody conjugates were prepared as described in International Patent Application No. PCT/US12/36795.

Tubes containing samples were loosely covered with parafilm and incubated for 30 minutes at 37° C. in a humidified incubator (5% $CO_2$). After incubation, all samples were washed two times with 2 mL of 1×DPBS and centrifuged at 1500-1700 rpm at 4° C. for five minutes. After aspiration, 5 µL of the anti-β-glucan antibody MD IV (Biothera, Inc., Eagan, Minn.; U.S. Pat. No. 6,294,321), was mixed into each tube and incubated at room temperature for 30 minutes. This antibody was washed twice and a cocktail of antibodies containing the secondary Ab FITC-conjugated goat anti-mouse IgM (Southern Biotech; Birmingham, Ala.) as well as the specific cell surface markers, CD15, CD14, CD19, CD3 and CD45 (Biolegend, San Diego, Calif.) were added and incubated for 30 minutes at room temperature in the dark. To lyse the red blood cells, 2 mL of 1× BD Lysing solution (BD Bioscience; San Jose, Calif.) was added to each sample and vortexed. After incubating at room temperature for 30 minutes the samples were centrifuged as described above and the pellet was washed with 2 mL 1×DPBS. Cells were fixed with 300 µL of 1% paraformaldehyde and acquired on the LSR II (BD Biosciences, San Jose, Calif.). Data was analyzed with FlowJo software (Tree Star, Ashland, Oreg.). The cells were assessed for their capacity to bind PGG by comparing the median fluorescence intensity (MFI) of the cells stained with BID IV and the percentage of cells positive for BfD IV relative to that of the vehicle treated control group.

EXEMPLARY EMBODIMENTS

Embodiment 1

A composition comprising:
a soluble β-glucan component; and
an antibody component that specifically binds to the soluble β-glucan.

Embodiment 2

The composition of Embodiment 1 wherein the soluble β-glucan is derived from yeast.

Embodiment 3

The composition of Embodiment 1 or Embodiment 2 wherein the soluble β-glucan comprises a β-1,3/1,6 glucan.

Embodiment 4

The composition of any preceding Embodiment wherein the soluble β-glucan comprises β(1,6)-[poly-(1,3)-D-glucopyranosyl]-poly-β(1,3)-D-glucopyranose.

Embodiment 5

The composition of any preceding Embodiment wherein the antibody component comprises a monoclonal antibody that specifically binds to the soluble β-glucan.

Embodiment 6

The composition of Embodiment 5 wherein the monoclonal antibody comprises BfD I, BfD II, BfD III, or BID IV.

Embodiment 7

The composition of any preceding Embodiment wherein the soluble β-glucan component and the antibody component are provided in a single formulation.

Embodiment 8

The composition of any preceding Embodiment wherein the soluble β-glucan component and the antibody component are provided in separate formulations.

Embodiment 9

The composition of any preceding Embodiment and further comprising an anti-tumor antibody.

Embodiment 10

A method comprising co-administering to a subject a soluble β-glucan and an antibody preparation or antibody component that specifically binds to the soluble β-glucan.

Embodiment 11

A method of increasing a subject's response to soluble β-glucan immunotherapy, the method comprising co-administering to the subject a composition that comprises a soluble β-glucan and an antibody preparation that specifically binds to the soluble β-glucan.

Embodiment 12

The method of Embodiment 11 further comprising identifying the subject as a low binder of β-glucan.

Embodiment 13

The method of any one of Embodiments 10-12 wherein the soluble β-glucan and the antibody preparation are co-administered simultaneously.

Embodiment 14

The method of any one of Embodiments 10-12 wherein the soluble β-glucan and the antibody preparation are co-administered at different times.

Embodiment 15

The method of any one of Embodiments 10-12 wherein the soluble β-glucan and the antibody preparation are co-administered at different sites.

Embodiment 16

The method of any one of Embodiments 10-15 wherein the soluble β-glucan is derived from yeast.

Embodiment 17

The method of any one of Embodiments 10-16 wherein the soluble β-glucan comprises a β-1,3/1,6 glucan.

Embodiment 18

The method of any one of Embodiments 10-17 wherein the soluble β-glucan comprises β(1,6)-[poly-(1,3)-D-glucopyranosyl]-poly-β(1,3)-D-glucopyranose.

Embodiment 19

The method of any one of Embodiments 10-18 wherein the antibody component comprises a monoclonal antibody that specifically binds to the β-glucan.

Embodiment 20

The method of Embodiment 19 wherein the monoclonal antibody comprises BfD I, BfD II, BfD III, or BfD IV.

Embodiment 21

A method of increasing a subject's response to soluble β-glucan immunotherapy, the method comprising administering to the subject a composition that comprises a soluble β-glucan moiety conjugated to an antibody or antibody fragment.

Embodiment 22

The method of Embodiment 21 and further comprising identifying the subject as a low binder of soluble β-glucan.

Embodiment 23

The method of Embodiment 21 or Embodiment 22 wherein the soluble β-glucan moiety is derived from yeast.

Embodiment 24

The method of Embodiments 21-23 wherein the soluble β-glucan moiety comprises, or is derived from, a β-1,3/1,6 glucan.

Embodiment 25

The method of any one of Embodiments 21-24 wherein the β-glucan moiety comprises, or is derived from, β(1,6)-[poly-(1,3)-D-glucopyranosyl]-poly-β(1,3)-D-glucopyranose.

Embodiment 26

The method of any one of Embodiments 21-25 wherein the antibody comprises a therapeutic antibody.

Embodiment 27

The method of any one of Embodiments 21-26 and further comprising administering an anti-tumor antibody.

Embodiment 28

The method of Embodiment 27 wherein the anti-tumor antibody specifically binds to leukemic or lymphomic cells.

Embodiment 29

The method of Embodiment 27 wherein the anti-tumor antibody binds to cells of solid tumor.

Embodiment 30

A method of treating a tumor comprising co-administering to a subject having a tumor a composition that comprises:
a soluble β-glucan;
an antibody preparation that specifically binds to the soluble β-glucan; and
an anti-tumor antibody preparation.

Embodiment 31

The method of Embodiment 30 and further comprising identifying the subject as a low binder of soluble β-glucan.

The complete disclosure of all patents, patent applications, and publications, and electronically available material (including, for instance, nucleotide sequence submissions in, e.g., GenBank and RefSeq, and amino acid sequence submissions in, e.g., SwissProt, PIR, PRF, PDB, and translations from annotated coding regions in GenBank and RefSeq) cited herein are incorporated by reference in their entirety. In the event that any inconsistency exists between the disclosure of the present application and the disclosure(s) of any document incorporated herein by reference, the disclosure of the present application shall govern. The foregoing detailed description and examples have been given for clarity of understanding only. No unnecessary limitations are to be understood therefrom. The invention is not limited to the exact details shown and described, for variations obvious to one skilled in the art will be included within the invention defined by the claims.

Unless otherwise indicated, all numbers expressing quantities of components, molecular weights, and so forth used in the specification and claims are to be understood as being modified in all instances by the term "about." Accordingly, unless otherwise indicated to the contrary, the numerical parameters set forth in the specification and claims are approximations that may vary depending upon the desired properties sought to be obtained by the present invention. At the very least, and not as an attempt to limit the doctrine of equivalents to the scope of the claims, each numerical parameter should at least be construed in light of the number of reported significant digits and by applying ordinary rounding techniques.

Notwithstanding that the numerical ranges and parameters setting forth the broad scope of the invention are approximations, the numerical values set forth in the specific examples are reported as precisely as possible. All numerical values, however, inherently contain a range necessarily resulting from the standard deviation found in their respective testing measurements.

All headings are for the convenience of the reader and should not be used to limit the meaning of the text that follows the heading, unless so specified.

What is claimed is:

1. A method of increasing a subject's response to soluble β-glucan immunotherapy, the method comprising:
   identifying the subject as a low binder of β-glucan; and
   co-administering to the subject a composition that comprises:
   soluble β(1,6)-[poly-(1,3)-D-glucopyranosyl]-poly-β(1,3)-D-glucopyranose; and
   an antibody preparation that specifically binds to the soluble β(1,6)-[poly-(1,3)-D-glucopyranosyl]-poly-β(1,3)-D-glucopyranose.

2. A method of increasing a subject's response to soluble β-glucan immunotherapy, the method comprising administering to the subject a composition that comprises:
   a soluble β-glucan moiety comprising β(1,6)-[poly-(1,3)-D-glucopyranosyl]-poly-β(1,3)-D-glucopyranose; and
   an antibody or antibody fragment conjugated to the β-glucan moiety.

3. The method of claim 2 and further comprising identifying the subject as a low binder of soluble β-glucan.

4. The method of claim 2 wherein the antibody comprises a therapeutic antibody.

5. The method of claim 2 and further comprising administering an anti-tumor antibody.

6. The method of claim 5 wherein the anti-tumor antibody specifically binds to leukemic or lymphomic cells.

7. The method of claim 5 wherein the anti-tumor antibody binds to cells of solid tumor.

8. A method of treating a tumor comprising co-administering to a subject having a tumor a composition that comprises:
   soluble β(1,6)-[poly-(1,3)-D-glucopyranosyl]-poly-β(1,3)-D-glucopyranose;
   an antibody preparation that specifically binds to the soluble β(1,6)-[poly-(1,3)-D-glucopyranosyl]-poly-β(1,3)-D-glucopyranose; and
   an anti-tumor antibody preparation.

9. The method of claim 8 and further comprising identifying the subject as a low binder of soluble β-glucan.

10. The method of claim 1 wherein the soluble β(1,6)-[poly-(1,3)-D-glucopyranosyl]-poly-β(1,3)-D-glucopyranose and the antibody preparation are co-administered simultaneously.

11. The method of claim 1 wherein the soluble β(1,6)-[poly-(1,3)-D-glucopyranosyl]-poly-β(1,3)-D-glucopyranose and the antibody preparation are administered sequentially so that the soluble β(1,6)-[poly-(1,3)-D-glucopyranosyl]-poly-β(1,3)-D-glucopyranose and the antibody preparation are simultaneously bioavailable after both are administered.

12. The method of claim 1 wherein the soluble β(1,6)-[poly-(1,3)-D-glucopyranosyl]-poly-β(1,3)-D-glucopyranose and the antibody preparation are co-administered at different sites.

13. The method of claim 1 wherein the antibody preparation comprises a monoclonal antibody that specifically binds to β(1,6)-[poly-(1,3)-D-glucopyranosyl]-poly-β(1,3)-D-glucopyranose.

* * * * *